(12) United States Patent
Ghesu et al.

(10) Patent No.: US 12,106,549 B2
(45) Date of Patent: Oct. 1, 2024

(54) SELF-SUPERVISED LEARNING FOR ARTIFICIAL INTELLIGENCE-BASED SYSTEMS FOR MEDICAL IMAGING ANALYSIS

(71) Applicant: Siemens Healthineers AG, Frochheim (DE)

(72) Inventors: Florin-Cristian Ghesu, Baiersdori (DE); Bogdan Georgescu, Princeton, NJ (US); Awais Mansoor, Potomac, MD (US); Sasa Grbic, Plainsboro, NJ (US); Dorin Comaniciu, Princeton, NJ (US)

(73) Assignee: Siemens Healthineers AG, Forchheim (DE)

( * ) Notice: Subject to any disclaimer, the term of this patent is extended or adjusted under 35 U.S.C. 154(b) by 378 days.

(21) Appl. No.: 17/454,696

(22) Filed: Nov. 12, 2021

(65) Prior Publication Data
US 2023/0154164 A1   May 18, 2023

(51) Int. Cl.
*G06V 10/774* (2022.01)
*G06V 10/82* (2022.01)
*G16H 30/40* (2018.01)

(52) U.S. Cl.
CPC .......... *G06V 10/7747* (2022.01); *G06V 10/82* (2022.01); *G16H 30/40* (2018.01)

(58) Field of Classification Search
None
See application file for complete search history.

(56) References Cited

U.S. PATENT DOCUMENTS

| | | | |
|---|---|---|---|
| 2021/0383225 A1* | 12/2021 | Grill | G06N 3/084 |
| 2023/0260652 A1* | 8/2023 | Azizi | G06T 7/0012 |
| | | | 382/128 |

OTHER PUBLICATIONS

Kingma et al., "Auto-Encoding Variational Bayes," 2013, arXiv preprint, 14 pgs.
Oord et al., "Neural Discrete Representation Learning," 2017, 31st Conference on Neural Information Processing Systems, 11 pgs.

(Continued)

*Primary Examiner* — Vincent Rudolph
*Assistant Examiner* — Leon Flores

(57) ABSTRACT

Systems and methods for training an artificial intelligence-based system using self-supervised learning are provided. For each respective training medical image of a set of unannotated training medical images, the following steps are performed. A first augmented image is generated by applying a first augmentation operation to the respective training medical image. A second augmented image is generated by applying a second augmentation operation to the respective training medical image. A first representation vector is created from the first augmented image using an encoder network. A second representation vector is created from the second augmented image using the encoder network. The first representation vector is mapped to first cluster codes. The second representation vector is mapped to second cluster codes. The encoder network is optimized using the first and second representation vectors and the first and second cluster codes.

20 Claims, 10 Drawing Sheets

(56) References Cited

OTHER PUBLICATIONS

Raghu et al., "Transfusion: Understanding Transfer Learning for Medical Imaging," 2019, 33rd Conference on Neural Information Processing Systems, 22 pgs.
Zhou, "A brief introduction to weakly supervised learning," 2018, National Science Review, vol. 5, Issue 1, pp. 44-53.
Zhou et al., "Models genesis: Generic autodidactic models for 3D medical image analysis," in Medical Image Computing and Computer Assisted Intervention, Eds. Cham: Springer International Publishing, 2019, pp. 384-393.
Zhuang et al., "Self-supervised Feature Learning for 3D Medical Images by Playing a Rubik's Cube," 2019, Medical Image Computing and Computer Assisted Intervention, pp. 420-428.
Chen et al., "Self-supervised learning for medical image analysis using image context restoration," Medical Image Analysis, vol. 58, p. 101539, 2019.
Caron et al., "Unsupervised Learning of Visual Features by Contrasting Cluster Assignments," 2020, 34th Conference on Neural Information Processing Systems, 13 pgs.
Caron et al., "Deep Clustering for Unsupervised Learning of Visual Features," 2018, Proceedings of the European Conference on Computer Vision (ECCV), pp. 132-149.
Philipsen et al., "Localized Energy-Based Normalization of Medical Images: Application to Chest Radiography," 2015, IEEE Transactions on Medical Imaging, vol. 34, Issue 9, pp. 1965-1975.
Dosovitskiy et al., "You Only Train Once: Loss-Conditional Training of Deep Networks," 2019, International Conference on Learning Representations, 17 pgs.
Yoon et al., "Federated Continual Learning with Weighted Interclient Transfer," 2021, Proceedings of the 38th International Conference on Machine Learning, pp. 12073-12086.
Nguyen et al., "Variational Continual Learning," 2017, 6th International Conference on Learning Representations, 18 pgs.
Caron et al., "Unsupervised learning of visual features by contrasting cluster assignments," in Advances in Neural Information Processing Systems, H. Larochelle, M. Ranzato, R. Hadsell, M. F. Balcan, and H. Lin, Eds., vol. 33. Curran Associates, Inc., 2020, pp. 9912-9924.
Chen et al. "A simple framework for contrastive learning of visual representations," in International Conference on Machine Learning, ser. Proceedings of Machine Learning Research, H. D. III and A. Singh, Eds., vol. 119. PMLR, 2020, pp. 1597-1607.
Deng et al., "ImageNet: A large-scale hierarchical image database," in IEEE Conference on Computer Vision and Pattern Recognition, 2009, pp. 248-255.
Nguyen et al., "Self-supervised learning based on spatial awareness for medical image analysis," IEEE Access, vol. 8, pp. 162 973-162 981, 2020.
Chaitanya et al., "Contrastive learning of global and local features for medical image segmentation with limited annotations," in Advances in Neural Information Processing Systems, Eds., vol. 33. Curran Associates, Inc., 2020, pp. 12546-12558.
Jiao et al., "Self-supervised representation learning for ultrasound video," in IEEE International Symposium on Biomedical Imaging, 2020, pp. 1847-1850.
Hadsell et al., "Dimensionality reduction by learning an invariant mapping," in IEEE Conference on Computer Vision and Pattern Recognition, vol. 2, 2006, pp. 1735-1742.
Wang et al., "ChestX-Ray8: Hospital-scale chest x-ray database and benchmarks on weakly-supervised classification and localization of common thorax diseases," in IEEE Conference on Computer Vision and Pattern Recognition, 2017, pp. 3462-3471.
Gundel et al., "Robust classification from noisy labels: Integrating additional knowledge for chest radiography abnormality assessment," Medical Image Analysis, vol. 72, p. 102087, 2021.
Dosovitskiy et al., "Discriminative unsupervised feature learning with convolutional neural networks," in Advances in Neural Information Processing Systems, Eds., vol. 27. Curran Associates, Inc., 2014.
Bojanowski et al. "Unsupervised learning by predicting noise," in International Conference on Machine Learning. JMLR.org, 2017, p. 517-526.
Wu et al., "Unsupervised feature learning via non-parametric instance discrimination," in IEEE Conference on Computer Vision and Pattern Recognition, 2018, pp. 3733-3742.
Gutmann et al. "Noise-contrastive estimation: A new estimation principle for unnormalized statistical models," in International Conference on Artificial Intelligence and Statistics, Eds., vol. 9. PMLR, 2010, pp. 297-304.
Zhuang et al. "Local aggregation for unsupervised learning of visual embeddings," in IEEE International Conference on Computer Vision, 2019, pp. 6001-6011.
He et al., "Momentum contrast for unsupervised visual representation learning," in IEEE Conference on Computer Vision and Pattern Recognition, 2020, pp. 9726-9735.
Hjelm et al., "Learning deep representations by mutual information estimation and maximization," in International Conference on Learning Representations, 2019.
Bachman et al., "Learning representations by maximizing mutual information across views," in Advances in Neural Information Processing Systems, Eds., vol. 32. Curran Associates, Inc., 2019.
Tian et al. "Contrastive multiview coding," in European Conference on Computer Vision, Eds. Cham: Springer International Publishing, 2020, pp. 776-794.
Henaff et al. "Data-efficient image recognition with contrastive predictive coding," in International Conference on Machine Learning, ser. Proceedings of Machine Learning Research, vol. 119. PMLR, 2020, pp. 4182-4192.
Bautista et al., "Cliquecnn: Deep unsupervised exemplar learning," in Advances in Neural Information Processing Systems, Eds., vol. 29. Curran Associates, Inc., 2016.
Caron et al., "Deep clustering for unsupervised learning of visual features," in European Conference on Computer Vision, Eds. Cham: Springer International Publishing, 2018, pp. 139-156.
Gidaris et al., "Unsupervised representation learning by predicting image rotations," in International Conference on Learning Representations, 2018.
Caron et al., "Unsupervised pretraining of image features on non-curated data," in IEEE International Conference on Computer Vision. IEEE Computer Society, 2019, pp. 2959-2968.
Yan et al., "ClusterFit: Improving generalization of visual representations," in IEEE Conference on Computer Vision and Pattern Recognition, 2020, pp. 6508-6517.
Huang et al., "Unsupervised deep learning by neighbourhood discovery," in International Conference on Machine Learning, ser. Proceedings of Machine Learning Research, Eds., vol. 97. PMLR, 2019, pp. 2849-2858.
Asano et al. "Self-labelling via simultaneous clustering and representation learning," in International Conference on Learning Representations, 2020.
Noroozi et al., "Unsupervised learning of visual representations by solving jigsaw puzzles," in European Conference on Computer Vision, Eds. Springer International Publishing, 2016, pp. 69-84.
Kim et al., "Learning image representations by completing damaged jigsaw puzzles," in IEEE Winter Conference on Applications of Computer Vision. IEEE Computer Society, 2018, pp. 793-802.
Agrawal et al., "Learning to see by moving," in IEEE International Conference on Computer Vision. USA: IEEE Computer Society, 2015, p. 37-45.
Misra et al., "Shuffle and learn: Unsupervised learning using temporal order verification," in European Conference on Computer Vision, B. Leibe, J. Matas, N. Sebe, and M. Welling, Eds. Cham: Springer International Publishing, 2016, pp. 527-544.
Zhou et al., "A boosting regression approach to medical anatomy detection," in IEEE Conference on Computer Vision and Pattern Recognition, 2007, pp. 1-8.
Doersch et al., "Unsupervised visual representation learning by context prediction," in IEEE International Conference on Computer Vision. USA: IEEE Computer Society, 2015, p. 1422-1430. [Online]. Available: https://doi.org/10.1109/ICCV.2015.167.

(56) References Cited

OTHER PUBLICATIONS

Pathak et al., "Context encoders: Feature learning by inpainting," in IEEE Conference on Computer Vision and Pattern Recognition, 2016, pp. 2536-2544.
Larsson et al., "Learning representations for automatic colorization," in European Conference on Computer Vision, Eds. Cham: Springer International Publishing, 2016, pp. 577-593.
Navarro et al., "Evaluating the robustness of self-supervised learning in medical imaging," 2021.
Azizi et al., "Big self-supervised models advance medical image classification," 2021.
Kim et al., "On single source robustness in deep fusion models," in Advances in Neural Information Processing Systems, Eds., vol. 32. Curran Associates, Inc., 2019.
Cuturi, "Sinkhorn distances: Lightspeed computation of optimal transport," in Advances in Neural Information Processing Systems, Eds., vol. 26. Curran Associates, Inc., 2013, pp. 1-11.
Philipsen et al., "Localized energy-based normalization of medical images: Application to chest radiography," IEEE Transactions on Medical Imaging, vol. 34, No. 9, pp. 1965-1975, 2015.
Johnson et al. "MIMIC-CXR, a deidentified publicly available database of chest radiographs with free-text reports," Scientific data, vol. 6, No. 1, pp. 1-8, 2019.
Goldberger et al., "PhysioBank, PhysioToolkit, and PhysioNet: components of a new research resource for complex physiologic signals," circulation, vol. 101, No. 23, pp. e215-e220, 2000.
Rosenthal et al., "The TB portals: an open-access, webbased platform for global drug-resistant-tuberculosis data sharing and analysis," Journal of Clinical Microbiology, vol. 55, No. 11, pp. 3267-3282, 2017.
D. Demner-Fushman et al., "Preparing a collection of radiology examinations for distribution and retrieval," Journal of the American Medical Informatics Association, vol. 23, No. 2, pp. 304-310, 2016.
Bustos et al., "Padchest: A large chest x-ray image dataset with multi-label annotated reports," Medical Image Analysis, vol. 66, p. 101797, 2020.
Armato et al., "The lung image database consortium (LIDC) and image database resource initiative (IDRI): a completed reference database of lung nodules on CT scans," Medical Physics, vol. 38, No. 2, pp. 915-931, 2011.
Jaeger et al., "Two public chest x-ray datasets for computer-aided screening of pulmonary diseases," Quantitative maging in medicine and surgery, vol. 4, No. 6, p. 475, 2014.
Halabi et al., "The RSNA pediatric bone age machine learning challenge," Radiology, vol. 290, No. 2, pp. 498-503, 2019.
Rajpurkar et al., "MURA: Large dataset for abnormality detection in musculoskeletal radiographs," 2018.
He et al., "Deep residual learning for image recognition," in IEEE Conference on Computer Vision and Pattern Recognition, 2016, pp. 770-778.
Rudolph et al., "Artificial intelligence in chest radiography reporting accuracy: Added clinical value in the emergency unit setting without 24/7 radiology coverage,"Investigative Radiology, 2021.
Rueckel et al., "Pneumothorax detection in chest radiographs: Optimizing artificial intelligence system for accuracy and confounding bias reduction using in-image annotations in algorithm training," European Radiology, pp. 7888-7900, 2021.
Barbosa et al., "Automated detection and quantification of COVID-19 airspace disease on chest radiographs: A novel approach achieving expert radiologist-level performance using a deep convolutional neural network trained on digital reconstructed radiographs from computed tomography—derived ground truth," Investigative radiology, 2021.

\* cited by examiner

FIG 6
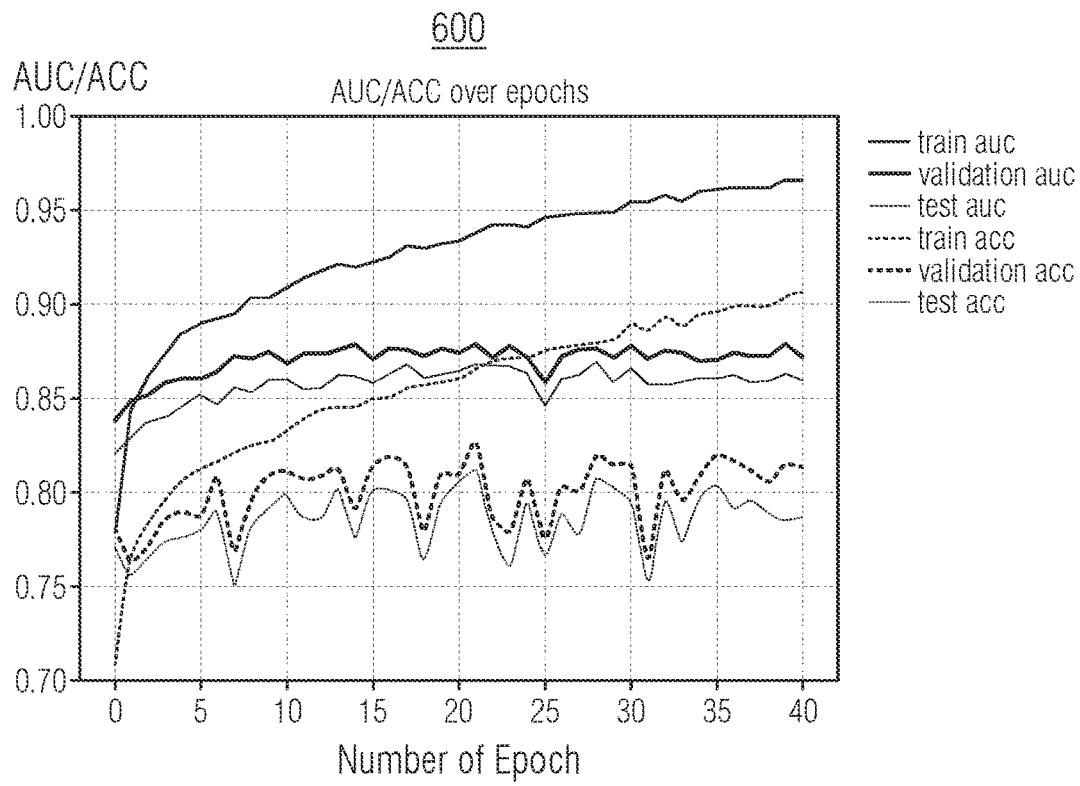
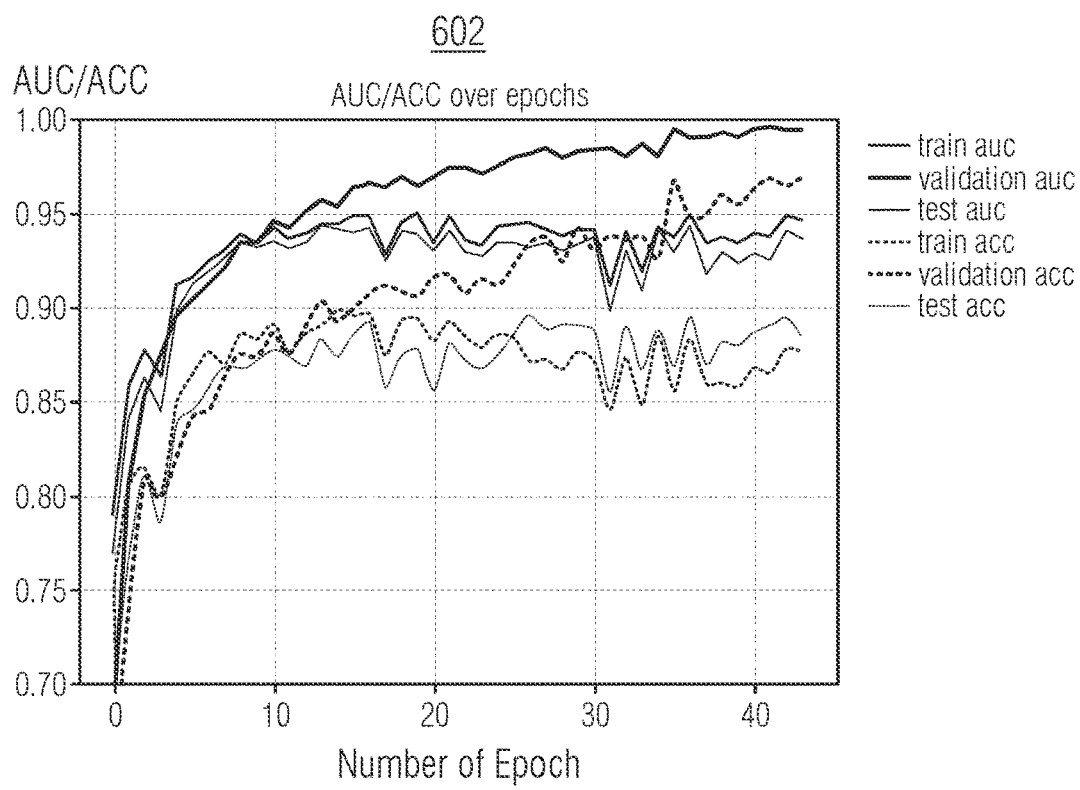

SELF-SUPERVISED LEARNING FOR ARTIFICIAL INTELLIGENCE-BASED SYSTEMS FOR MEDICAL IMAGING ANALYSIS

TECHNICAL FIELD

The present invention relates generally to training of artificial intelligence-based systems, and in particular to self-supervised learning for artificial intelligence-based systems for medical imaging analysis.

BACKGROUND

Often times, artificial intelligence-based systems are trained for medical imaging analysis (e.g., detection, segmentation, or classification of anatomies or abnormalities) on relatively small sets of training data. This often results in limited performance and generalizability on unseen data during the inference stage, as the appearance of certain anatomies and abnormalities is highly variable and may not be fully captured in such small datasets. While such artificial intelligence-based systems may be trained using relatively large sets of training data, the availability of such training data is limited due to strong privacy regulations and the high cost of annotating the training data.

BRIEF SUMMARY OF THE INVENTION

In accordance with one or more embodiments, systems and methods for training an artificial intelligence-based system using self-supervised learning are provided. For each respective training medical image of a set of unannotated training medical images, the following steps are performed. A first augmented image is generated by applying a first augmentation operation to the respective training medical image. A second augmented image is generated by applying a second augmentation operation to the respective training medical image. A first representation vector is created from the first augmented image using an encoder network. A second representation vector is created from the second augmented image using the encoder network. The first representation vector is mapped to first cluster codes. The second representation vector is mapped to second cluster codes. The encoder network is optimized using the first and second representation vectors and the first and second cluster codes.

In one embodiment, the encoder network is optimized to find cluster codes that maximize a similarity between representation vectors and cluster prototypes. The encoder network may be optimized by calculating a first loss based on the first representation vectors and the second cluster codes, calculating a second loss based on the second representation vectors and the first cluster codes, and combining the first loss and the second loss. In one embodiment, the encoder network is optimized by optimizing a loss function by clustering based on a modality of each of the training medical images.

In one embodiment, one of the first augmentation operation or the second augmentation operation comprises an energy-based augmentation. The energy-based augmentation is performed by decomposing an image into a plurality of energy bands, computing an energy value for each of the plurality of energy bands, and transforming the image based on the energy values. The set of unannotated training medical images may comprise a plurality of subsets of training medical images each associated with different sites. The encoder network may be continuously optimized with the plurality of subsets of training medical images using federated learning and continual learning.

In one embodiment, annotated training data comprising annotated training medical images and corresponding annotations is received. The annotated training medical images are mapped to predicted annotations using a machine learning based network based on features of the encoder network. The encoder network is optimized to minimize a distance of the predicted annotations to the corresponding annotations.

In one embodiment, an input medical image is received. A representation vector is created from the input medical image using the optimized encoder network. A medical imaging analysis task is performed for the input medical image based on the representation vector. Results of the medical imaging analysis task are output. In one embodiment, the medical imaging analysis task is performed by decoding the representation vector using a decoder network to perform the medical imaging analysis task. The medical imaging analysis task may comprise at least one of detection, segmentation, or classification of an anatomy or abnormality in the input medical image.

These and other advantages of the invention will be apparent to those of ordinary skill in the art by reference to the following detailed description and the accompanying drawings.

BRIEF DESCRIPTION OF THE DRAWINGS

FIG. 6 shows graphs comparing the performance of artificial intelligence-based systems trained using only annotations and the performance of artificial intelligence-based systems trained using annotations with self-supervised learning in accordance with embodiments described herein;

DETAILED DESCRIPTION

The present invention generally relates to methods and systems for self-supervised learning for artificial intelligence-based systems for medical imaging analysis. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Self-supervised learning is a type of learning using unlabeled training images. In accordance with embodiments described herein, self-supervised learning utilizes a set of arbitrary N-dimensional training medical images, which can scale to the thousands, millions, billions, or more. Certain embodiments described herein are based on the SWaV (swapping assignments between views) framework, but modified to jointly learn from multiple imaging modalities by a contrastive clustering loss function. Further, embodiments described herein provided for a hybrid self-supervised/supervised learning approach to incorporate annotations of annotated training images in the self-supervised learning framework. In some embodiments, self-supervised learning can be deployed in the context of federated learning and continual learning.

Training (or pretraining) of an artificial intelligence-based system, such as, e.g., a machine learning-based system, by self-supervised learning is described herein with respect to FIGS. 1-2 below. Such training of the artificial intelligence-based system is performed during a prior offline or training stage. Once trained, the trained artificial intelligence-based system is applied to perform a medical imaging analysis task (e.g., detection, segmentation, or classification of anatomies or abnormalities) during an online or inference stage, as described with respect to FIG. 3 below.

Figure 1:
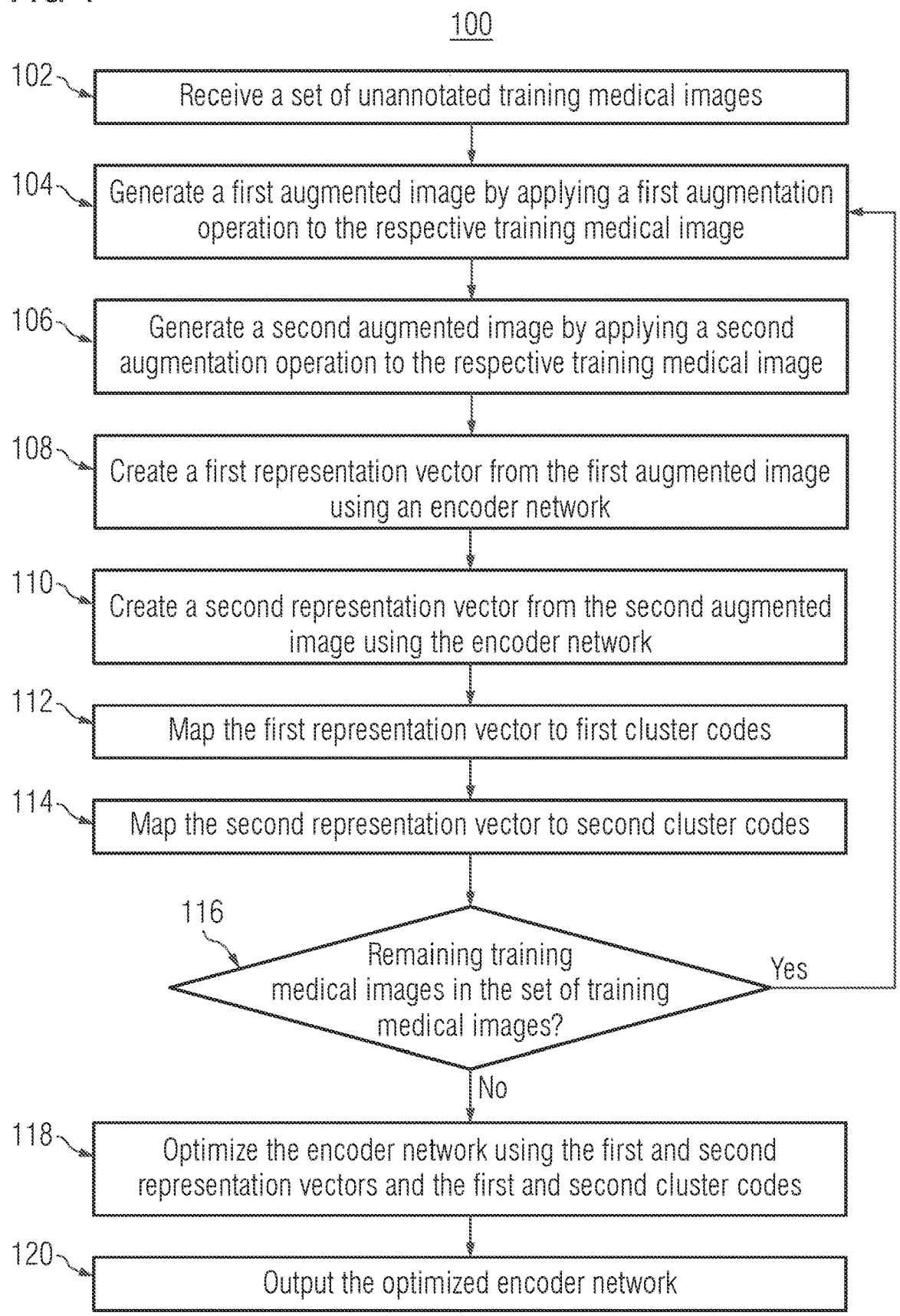
FIG. 1 shows a method for self-supervised learning for training an artificial intelligence-based system, in accordance with one or more embodiments.

FIG. 1 shows a method 100 for self-supervised learning for training an artificial intelligence-based system, in accordance with one or more embodiments. The steps of method 100 may be performed by one or more suitable computing devices, such as, e.g., computer 1002 of FIG. 10. Method 100 is performed during a prior offline or training stage. FIG. 2 shows a framework 200 for self-supervised learning for training an artificial intelligence-based system, in accordance with one or more embodiments. FIG. 1 and FIG. 2 will be described together.

At step 102 of FIG. 1, a set of unannotated (also referred to as unlabeled) training medical images is received. FIG. 2 shows an exemplary training medical input image I 202 sampled from a set of training medical images. The set of training medical images may comprise any number of unannotated training medical images. The set of training medical images may be a batch of training medical images from a larger set of training medical images. The training medical images may depict, for example, anatomy and/or abnormalities of a patient.

In one embodiment, the training medical images in the set are of a plurality of different modalities, such as, e.g., MRI (magnetic resonance imaging), CT (computed tomography), ultrasound, x-ray, and/or any other medical imaging modality or combinations of medical imaging modalities. The set of training medical images may comprise 2D (two dimensional) images and/or 3D (three dimensional) volumes, and each training medical image may comprise a single image or a plurality of images (e.g., channels). The set of training medical images may be received directly from an image acquisition device, such as, e.g., a CT scanner, as the training medical images are acquired, or can be received by loading previously acquired training medical images from a storage or memory of a computer system (e.g., a PACS (picture archiving and communication system)) or by receiving medical images that have been transmitted from a remote computer system.

Method 100 then proceeds to step 104 to perform steps 104-114 for a first respective training medical image in the set of unannotated training medical images.

At step 104 of FIG. 1, a first augmented image is generated by applying a first augmentation operation to the respective training medical image and, at step 106 of FIG. 1, a second augmented image is generated by applying a second augmentation operation to the respective training medical image. In one example, as shown in FIG. 2, a first augmented image $I_1$ 206 is generated by applying a first augmentation operation $t_1$ to training medical input image 1202 and a second augmented image $I_2$ 208 is generated by applying a second augmentation operation $t_2$ to training medical input image 1202. Augmentation operations $t_1$ and $t_2$ are selected from a set of augmentation operations T.

In one embodiment, the first augmentation operation and the second augmentation operation are different augmentation operations. By applying both the first augmentation operation and the second augmentation operation to the respective training medical image, different augmented images are generated that correlate with each other. The first augmentation operation and the second augmentation operation may be any suitable operation or operations for transforming the respective training medical image. The first augmentation operation and the second augmentation operation may comprise any other suitable augmentation operation, such as, e.g., 1) crop and resize to original resolution, 2) crop, resize to original resolution, and flip, 3) color distortion (drop), 4) color distortion (jitter), 5) rotation (e.g., 90 degrees, 180 degrees, 270 degrees), 6) cutout, 7) Gaussian noise, 8) Gaussian blur, 9) Sobel filtering, or a combination thereof. In one embodiment, the first augmentation operation and the second augmentation operation are compositional such that each operation comprises or is composed of a plurality of operations. For example, the first augmentation operation may comprise rotation, rescaling, intensity variation, and cropping and the second augmentation operation may comprise rotation and cropping.

In one embodiment, one of the first augmentation operation or the second augmentation operation comprises an energy-based augmentation where, based on different energy bands of the respective training medical image, statistics may be computed and used to vary the image reconstruction weighting factor on each band. In energy-based augmentation, an image I is decomposed into B energy bands $B^{(1)}, B^{(2)}, \ldots, B^{(B)}$ using Gaussian filtering. For each band $1 \leq i \leq B$, the energy value $e_i(I, \Omega)$ is computed as the brightness dispersion in a predefined image region defined by $\Omega$ (e.g., the entire image). Image I is then normalized to transform the image based on the energy values $e_i(I, \Omega)$ as follows:

$$\hat{I}(\Omega) = \sum_{i=1}^{B} \lambda_i(\Omega) I^{(i)} = \sum_{i=1}^{B} \frac{e_i^{ref}(\Omega)}{e_i(I, \Omega)} I^{(i)} \quad \text{(Equation 1)}$$

where $$e_i^{ref}(\Omega) = \frac{1}{R} \sum_{k=1}^{R} e_i(I_k, \Omega)$$

denotes the reference energy value on band i, with $I_1$, $I_2, \ldots, I_R$ denoting R preselected reference images. In one example, R is set to 1000 and image I is augmented using a variable reference energy $e_i^{ref}(\Omega)$ for any given band $1 \leq i \leq B$ around the mean value. On each band, the distribution of the band R reference value is modelled using a Gaussian distribution and the value of the reference energy is sampled from the range band $[-\sigma, +\sigma]$ around the mean energy value.

At step 108 of FIG. 1, a first representation vector is extracted from the first augmented image using an encoder network and, at step 110 of FIG. 1, a second representation vector is extracted from the second augmented image using the encoder network. In one example, as shown in FIG. 2, a first representation vector $Z_1$ 214 is extracted from the first augmented image $I_1$ 206 using encoder network $f_\theta$ 212 and a second representation vector $Z_2$ 216 is extracted from the second augmented image $I_2$ 210 using encoder network $f_\theta$ 212. While encoder network $f_\theta$ 212 is separately shown in FIG. 2 to separately illustrate the processing of first augmented image $I_1$ 206 and second augmented image $I_2$ 210, it should be understood that the same encoder network $f_\theta$ 212 is used to extract first representation vector $I_1$ 214 and second representation vector $I_2$ 216. This can be formally expressed as $Z_1 = f_\theta(I_1)$ and $Z_2 = f_\theta(I_2)$.

The encoder network may be any suitable machine learning-based network for respectively encoding the first and second augmented images to first and second representation vectors. In one example, the encoder network is a neural network, such as, a ResNet (Residual Network). The first and second representation vectors respectively comprise latent features of the first and second augmented images.

At step 112 of FIG. 1, the first representation vector is mapped to first cluster codes and, at step 114 of FIG. 1, the second representation vector is mapped to second cluster codes. In one example, as shown in FIG. 2, first representation vector $Z_1$ 214 is mapped to first cluster codes $Q_1$ 220 from a set of cluster prototypes C 218 and second representation vector $Z_2$ 216 is mapped to second cluster codes $Q_2$ 222 from the set of cluster prototypes C 218. This can be formally expressed as $Q_1 = g(Z_1)$ and $Q_2 = g(Z_2)$, where $g(\cdot)$ is the projection network. The first cluster codes $Q_1$ 220 and second cluster codes $Q_2$ 222 are features of the first representation vector $Z_1$ 214 and the second representation vector $Z_2$ 216 respectively in a feature space where a contrastive clustering loss function is applied (at step 118).

The projection network may be any suitable machine learning-based network for respectively mapping the first and second representation vectors to first and second cluster codes. In one example, the projection network is a neural network, such as, e.g., an MLP (multilayer perceptron).

Method 100 of FIG. 1 then proceeds to decision block 116, where it is determined whether there are any remaining training medical images in the set of training medical images. If there are remaining training medical images in the set of training medical images, then method 100 returns to step 104 and steps 104-114 are performed for a next respective training medical image. Accordingly, steps 104-114 are performed for each respective training medical images in the set of training medical images. If there are no remaining training medical images in the set of training medical images, method 100 proceeds to step 118. The set of training medical images may represent a batch of training medical images for training the encoder network.

At step 118 of FIG. 1, the encoder network is optimized using the first and second representation vectors and the first and second cluster codes. The encoder network is optimized according to a contrastive loss function based on swapped predictions, such that the loss is calculated based on a first loss calculated based on the first representation vector and the second cluster codes, a second loss calculated based on the second representation vector and the first cluster codes, and the overall loss is calculated by combining (e.g., adding) the first loss and the second loss. Formally, this is expressed as $L(Z_1, Z_2) = l(Z_1, Q_2) + l(Z_2, Q_1)$, where Z represents a representation vector and Q represents cluster codes. The encoder network is optimized to find cluster codes Q that maximize the similarity between the representation vectors Z and cluster prototypes C according to the following loss function:

$$\max_{Q \in Q} Tr(Q^T C^T Z) + \epsilon H(Q) \qquad \text{(Equation 2)}$$

where H is entropy and E is a regularization weighing factor. The solution Q* to Equation 2 can be determined as a normalized exponential matrix using the Sinkhorn-Knopp algorithm. In one example, as shown in FIG. 2, encoder network $f_\theta$ 212 is optimized based on swapped prediction optimization 224 by optimizing cluster codes $Q_1$ 220 and $Q_2$ 222 to maximize the similarity between representation vectors $Z_1$ 214 and $Z_2$ 216 and cluster prototypes C 218. By optimizing the encoder network based on swapped predictions, features are obtained that are robust to the first and second augmentation operations.

In local experiments, pretraining on 1.8 million x-ray images or pretraining on 105 million CT/MR/ultrasound/x-ray images yielded a considerable increase in performance in assessing chest x-ray abnormalities based on a downstream task on 12 thousand images (1-3% AUC (area under the curve) increase compared to transfer learning and up to 12% increase in AUC compared to no pretraining), significantly increased training speed, and provided a consistent increase in robustness to various input augmentations (e.g., rotation, scaling, intensity variations, etc.).

Equation 2 may be used to learn from a multi-modality dataset of training medical images using random sampling. However, in one embodiment, the loss function of Equation 2 is modified to a contrastive clustering loss function that conditions clustering based on a modality of the training medical images. Specifically, cluster prototypes $C_m$ are clustered according to different modalities m according to the following contrastive clustering loss function:

$$\sum_{m=1}^{M} \max_{Q_m \in Q} Tr(Q_m^T C_m^T Z^{(m)}) + \epsilon H(Q_m) \qquad \text{(Equation 3)}$$

where $Q_m$ and $C_m$ are conditioned on modality m and $Z^{(m)}$ denotes the aggregate of $$\frac{B}{M}$$

vectors z associated with modality m.

At step 120 of FIG. 1, the optimized encoder network is output. For example, the optimized encoder network can be output by storing the optimized encoder network on a memory or storage of a computer system, or by transmitting the optimized encoder network to a remote computer system. The optimized encoder network may be applied during an online or inference stage for performing a medical imaging analysis task on an input medical image. In one embodiment, method 100 may be repeated for addition sets of training medical images representing additional batches.

Figure 3:
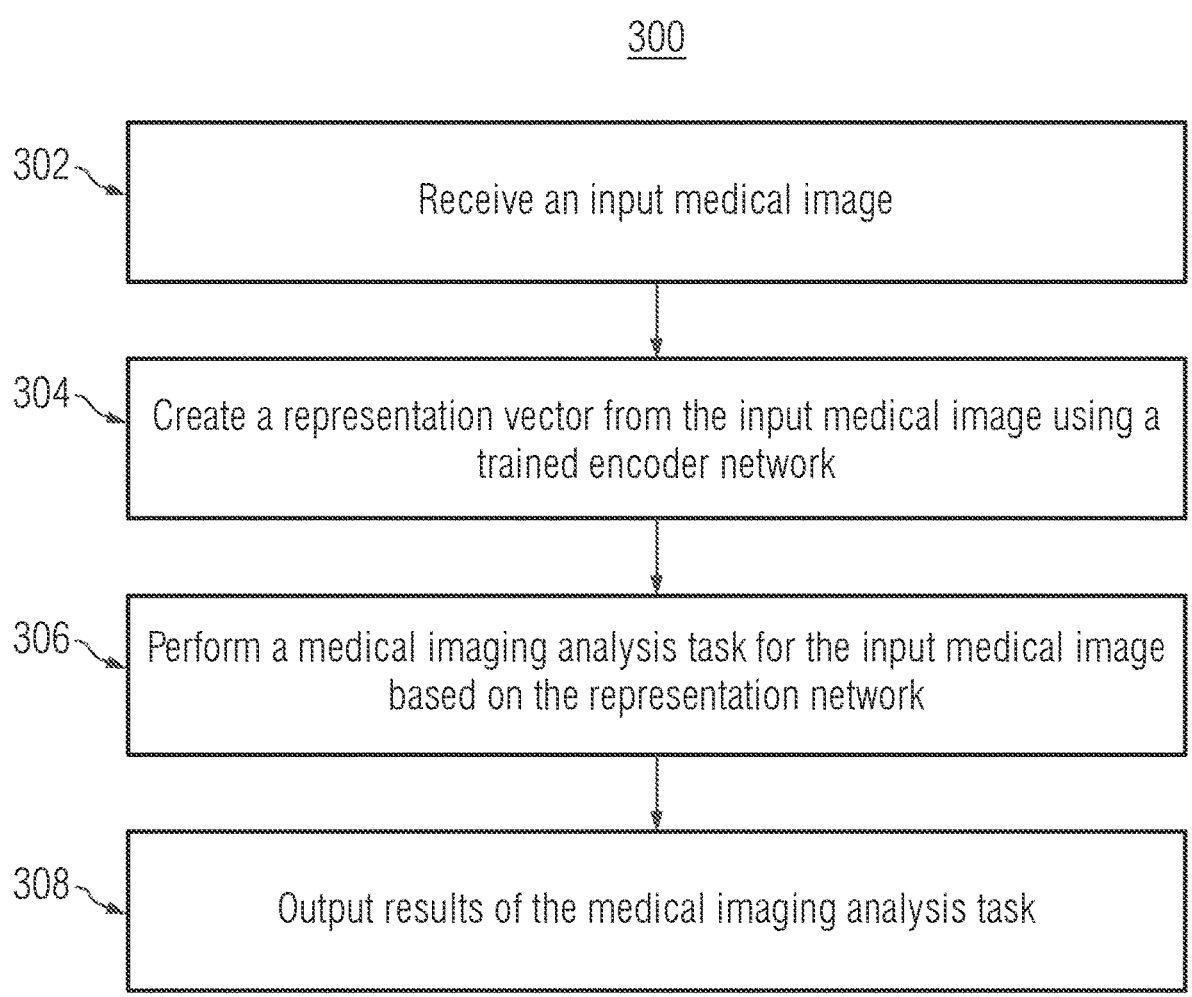
FIG. 3 shows a method for performing a medical imaging analysis task using a trained encoder network, in accordance with one or more embodiments.

FIG. 3 shows a method 300 for performing a medical imaging analysis task using a trained encoder network, in accordance with one or more embodiments. The steps of method 300 may be performed by one or more suitable computing devices, such as, e.g., computer 1002 of FIG. 10. Method 300 is performed during an online or inference stage.

At step 302, an input medical image is received. The input medical image may depict, for example, anatomies and/or abnormalities of a patient. The input medical image may be of any suitable modality, such as, e.g., MRI, CT, ultrasound, x-ray, and/or any other medical imaging modality or combinations of medical imaging modalities. The input medical image may comprise 2D (two dimensional) images and/or 3D (three dimensional) volumes, and may comprise a single input medical image or a plurality of input medical images. The input medical image may be received directly from an image acquisition device, such as, e.g., a CT scanner, as the input medical image is acquired, or can be received by loading a previously acquired input medical image from a storage or memory of a computer system (e.g., a PACS (picture archiving and communication system)) or by receiving an input medical image that have been transmitted from a remote computer system.

At step 304, a representation vector is extracted from the input medical image using a trained encoder network. In one embodiment, the trained encoder network is the encoder network optimized according to method 100 of FIG. 1. The representation vector comprises latent features of the input medical image. The encoder network may be any suitable machine learning-based network for encoding the input medical image to the representation vector. In one example, the encoder network is a neural network, such as, e.g., a ResNet.

At step 306, a medical imaging analysis task is performed for the input medical image based on the representation vector. The medical imaging analysis task may be any task for analyzing the input medical image, such as, e.g., detection, segmentation, or classification of anatomies and/or abnormalities in the input medical image. In one embodiment, a decoder network is applied to decode the representation vector to perform the medical imaging analysis task. The encoder network may be reused for other medical imaging analysis tasks, for example, using transfer learning (i.e., pretraining) where training is continuously performed in a supervised way on a specific downstream task. For downstream tasks, more complex models may also be utilized and embodiments described herein are not limited to an encoder network. For example, self-supervised learning may be used to pretrain a backbone network (residual network based).

At step 308, results of the medical imaging analysis task are output. The results of the medical imaging analysis task may comprise, for example, a probability map, a segmentation map, a classification, etc. The results of the medical imaging analysis task can be output by displaying the results of the medical imaging analysis task on a display device of a computer system, storing the results of the medical imaging analysis task on a memory or storage of a computer system, or by transmitting the results of the medical imaging analysis task to a remote computer system.

Figure 4:
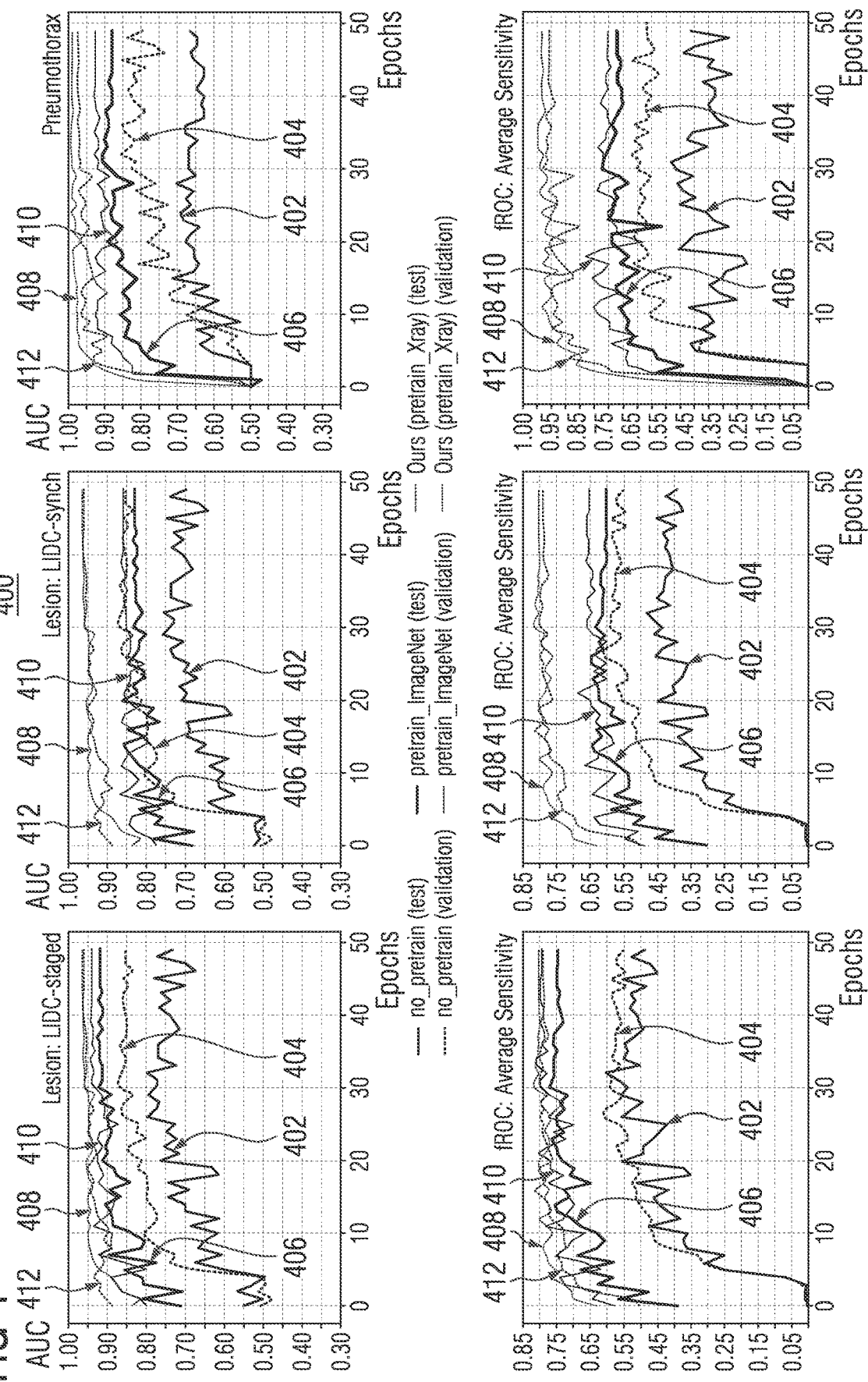
FIG. 4 shows a graph comparing performance of conventional artificial intelligence-based systems with an artificial intelligence-based system pretrained according to the self-supervised learning in accordance with embodiments described herein.

FIG. 4 shows graphs 400 comparing performance for lesion and pneumothorax detection in chest radiographs of conventional artificial intelligence-based systems with an artificial intelligence-based system pretrained according to the self-supervised learning in accordance with embodiments described herein. Graphs 400 compare AUC over time (in Epochs) and average instance-level sensitivity over time. Lines 402 and 404 respectively represent testing and validation performance of conventional artificial intelligence-based systems that are not pretrained. Lines 406 and 408 respectively represent testing and validation performance of conventional pretrained ImageNet. Lines 410 and 412 respectively represent testing and validation performance of an artificial intelligence-based system pretrained according to the self-supervised learning in accordance with embodiments described herein. The artificial intelligence-based system pretrained according to the self-supervised learning in accordance with embodiments described herein outperform both conventional approaches in terms of AUC and average instance detection sensitivity. The difference is significant, ranging between 3-5%. The difference is much larger when compared to using no pretraining, ranging between 20-25% on the lesion test and reaching almost 30% on the very challenging pneumothorax test data.

Figure 5:
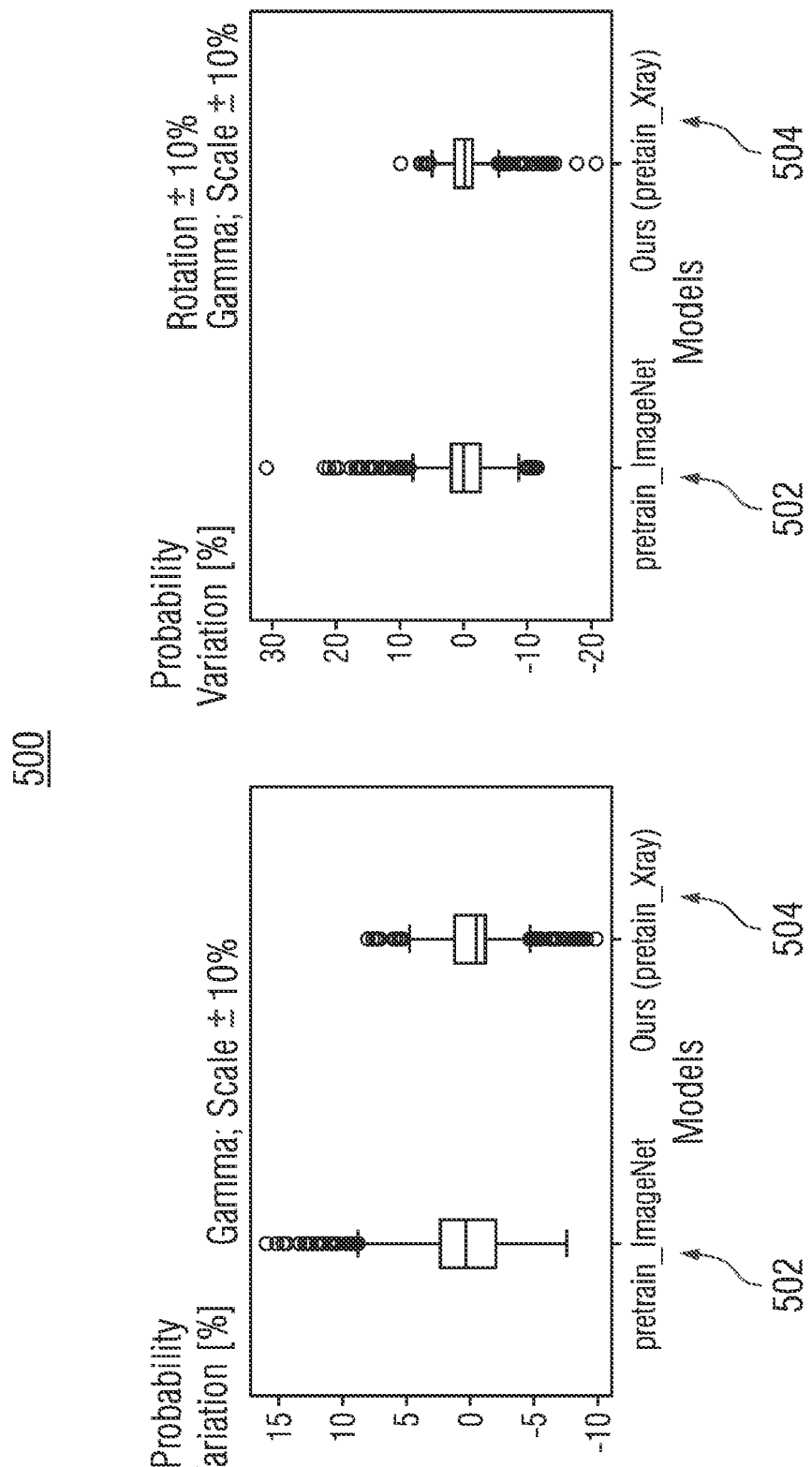
FIG. 5 shows a graph illustrating the robustness of an artificial intelligence-based system pretrained according to the self-supervised learning in accordance with embodiments described herein.

FIG. 5 shows a graph 500 illustrating the robustness of an artificial intelligence-based system pretrained according to the self-supervised learning in accordance with embodiments described herein. Box plot 502 represents probability variation of a conventional pretrained ImageNet. Box plot 504 represents probability variation of artificial intelligence-based system trained according to the self-supervised learning in accordance. As shown in graph 500, using the self-supervised learning (box plot 504) yields a higher level of robustness relative to standard augmentations.

In one embodiment, where at least some of the training medical images of the set of training medical images are annotated (e.g., with image level labels, annotation masks, bounding boxes, associated text descriptions), the annotations may be exploited and incorporated into the self-supervised learning framework. In one embodiment, annotated training images may be incorporated into the self-supervised learning framework by, for example, adding a new auxiliary loss to the optimization of the encoder network (at step 118 of FIG. 1), by a loss-conditional training, or by using an alternating learning strategy (i.e., alternating between self-supervised learning and supervised learning based on the annotations). In one embodiment, a hybrid self-supervised—supervised learning approach provided for dynamically incorporating annotations in the self-supervised learning framework. Given dataset $\mathcal{D} = [x_1, x_2, \ldots, x_{N'}, (x_{N'+1}, y_{N'+1}), \ldots, (x_N, y_N)]$ of N training samples, N-N' samples are paired with annotations or labels $y_k$ (where k>N'). Let $g_\omega$ be a deep neural network projector parameterized by $\omega$. Annotated samples $x_k$ are mapped to predicted annotations $\hat{y}_k$ from features of encoder network $f_\theta$ (output features and/or intermediate layer features) is as follows:

$$\hat{y}_k = g_\omega(x_k | f_\theta), \forall_k > N'$$

In this case, to optimize the encoder network $f_\theta$, the goal is similar to any supervised learning problem, i.e., minimize the distance of predicted label $\hat{y}_k$ to label $y_k$ according to a loss function $\mathcal{L}_{sup}$ (sup=supervised):

$$[\theta^*, \omega^*] = \operatorname*{argmin}_{\theta, \omega} \frac{1}{N - N'} \sum_{k=N'+1}^{N} \mathcal{L}_{sup}[g_\omega(x_k | f_\theta), y_k].$$

Combining equations to a single global optimization criterion and re-balancing the contribution of each using factors $\alpha, \beta \in \mathbb{R}$ gives the following objective for optimizing the encoder network:

$$[\theta^*, \omega^*, C^*] = \underset{\theta, \omega, C}{\mathrm{argmin}}\, \frac{1}{N}\sum_{k=1}^{N} \alpha \mathcal{L}_{sss}(x_k) + 1_{k>n'}\beta \mathcal{L}_{sup}[g_\omega(x_k \mid f_\theta), y_k].$$

Experiments incorporating annotated training medical images in self-supervised learning have shown improved performance in the downstream medical imaging analysis task. FIG. 6 shows graphs comparing the performance of artificial intelligence-based systems trained using only annotations and the performance of artificial intelligence-based systems trained using annotations with self-supervised learning in accordance with embodiments described herein. Graph 600 shows AUC and ACC (accuracy) for validating and testing of artificial intelligence-based system trained only with training medical images annotated with hemorrhage labels. The AUC for validating was found to be 0.88 and the AUC for testing was found to be 0.87. Graph 602 shows AUC and ACC for validating and testing of artificial intelligence-based system trained with training medical images annotated with hemorrhage labels, types, and slice labels with self-supervised learning. The AUC for validating was found to be 0.95 and the AUC for testing was found to be 0.94. Accordingly, performance of artificial intelligence-based systems increased from 0.87 to 0.94 AUC when trained with annotated training medical images with self-supervised learning.

Figure 7:
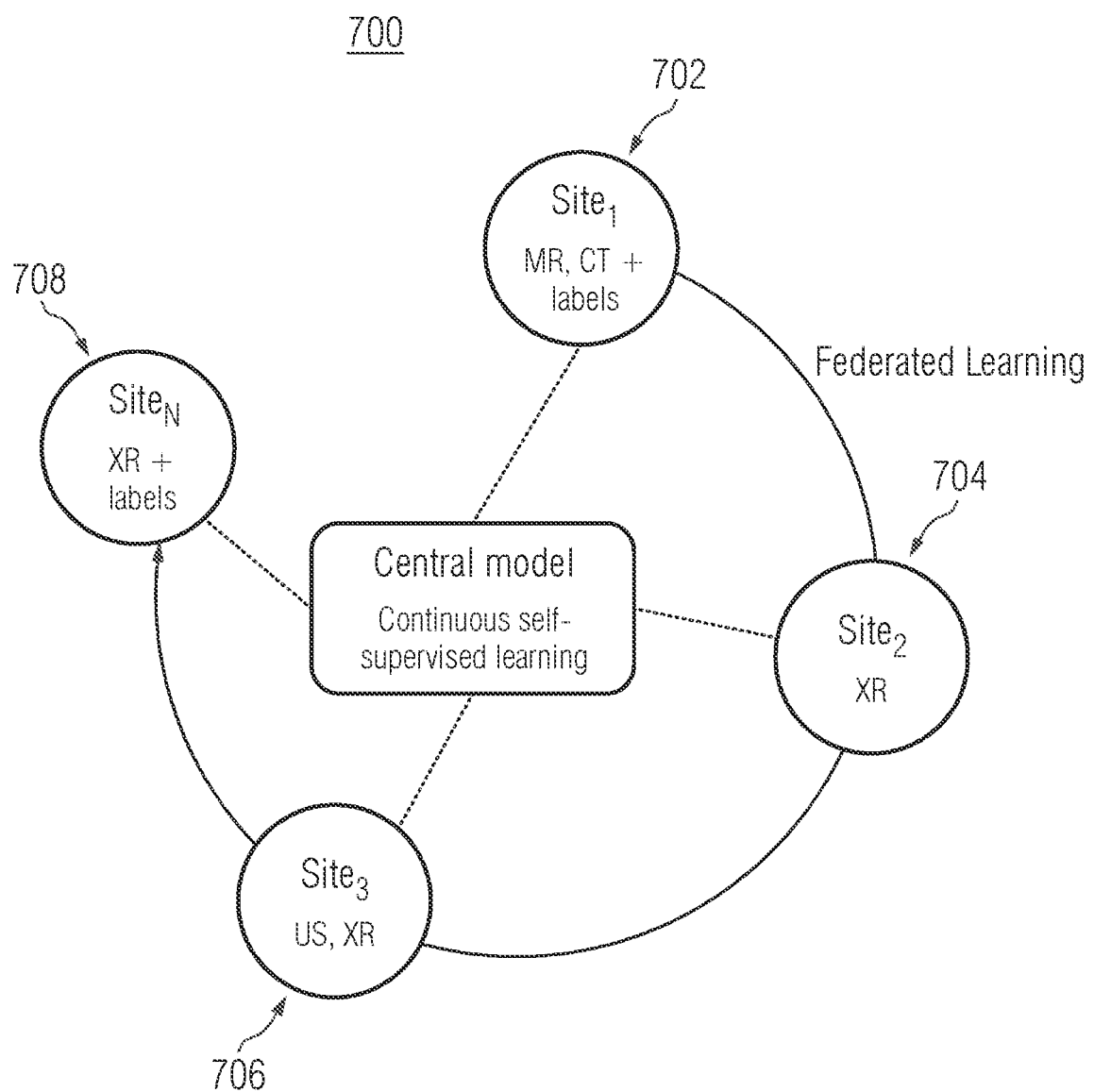
FIG. 7 shows a framework for self-supervised learning performed with federated learning, in accordance with one or more embodiments.

FIG. 7 shows a framework 700 for self-supervised learning performed with federated learning, in accordance with one or more embodiments. Federated learning is a machine learning technique that trains a machine learning algorithm across multiple decentralized devices holding local training data, without exchanging the local training data. In the context of medical imaging, coupling self-supervised learning with federated learning brings a number of advantages. Federated self-supervised learning naturally scales to large pools of data (ranging up to billions of images), while avoiding stringent data privacy regulations by accessing the data on site and training the machine learning algorithm on site. Federated self-supervised learning may provide a more effective strategy to control the learning strategy based on the quality of local annotations. For example, if a certain site provides low quality annotations, the system learns from the local training data of that site in a purely self-supervised way (i.e., without annotations). Further, in federated self-supervised learning, training from different sites may be weighted based on the downstream medical imaging analysis task.

FIG. 7 shows a plurality of sites comprising Site$_1$ 702, Site$_2$ 704, Site$_3$ 706, and Site$_N$ 708, each offering subsets of training medical images in different modalities, with or without annotations, and with or without non-imaging data (e.g., clinical reports, laboratory data, etc.). In practice, access to each site, and their associated training medical data, is not perpetual. If it would be, training central machine learning model 710 would be possible using a number of different approaches for federated learning. However, access to certain sites can be lost or gained. In accordance with one embodiment, central model 710 is trained with self-supervised learning combined with federated learning and continual learning. Federated learning allows for centralized training of central model 710 from training data from sites 702-708. Continual learning allows for continual learning of central model 710 without forgetting what the model has already learned, even when access to one or more using sites 702-708 is lost. Accordingly, central model 710 may be trained using self-supervised learning with federated learning and continual learning using training data of all sites 702-208 over time, while not losing information learned from sites once access to those sites is lost, and while learning from training medical images from new sites. Since the central model 710 is continually updated by different sites, gaining or losing access to a certain site does not impact the knowledge already gained by the system. Furthermore, the amount of knowledge gained by central model 710 from a specific site can be modulated based on the task for central model (e.g., if central model 710 is tasked to label regions in XR images, Site$_1$ 702 will be weighed less than the other sites). Continual learning may be implemented via Bayesian inference to address the diversity of data from different datasets. In addition, the so called coreset may be modelled using generative replay to achieve stability in the modeling of the posterior after observing T-1 datasets, while properly capturing the information encoded in dataset T as a likelihood $p(S_T|\theta)$, where $\theta$ represents the model parameters $p(\theta|S_1 \ldots _T) \propto p(\theta|S_1 \ldots _{T-1}) p(S_T|\theta)$.

Embodiments described herein are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the providing system.

Furthermore, certain embodiments described herein are described with respect to methods and systems utilizing trained machine learning based networks (or models), as well as with respect to methods and systems for training machine learning based networks. Features, advantages or alternative embodiments herein can be assigned to the other claimed objects and vice versa. In other words, claims for methods and systems for training a machine learning based network can be improved with features described or claimed in context of the methods and systems for utilizing a trained machine learning based network, and vice versa.

In particular, the trained machine learning based networks applied in embodiments described herein can be adapted by the methods and systems for training the machine learning based networks. Furthermore, the input data of the trained machine learning based network can comprise advantageous features and embodiments of the training input data, and vice versa. Furthermore, the output data of the trained machine learning based network can comprise advantageous features and embodiments of the output training data, and vice versa.

In general, a trained machine learning based network mimics cognitive functions that humans associate with other human minds. In particular, by training based on training data, the trained machine learning based network is able to adapt to new circumstances and to detect and extrapolate patterns.

In general, parameters of a machine learning based network can be adapted by means of training. In particular, supervised training, semi-supervised training, unsupervised training, reinforcement learning and/or active learning can be used. Furthermore, representation learning (an alternative term is "feature learning") can be used. In particular, the parameters of the trained machine learning based network can be adapted iteratively by several steps of training.

In particular, a trained machine learning based network can comprise a neural network, a support vector machine, a decision tree, and/or a Bayesian network, and/or the trained machine learning based network can be based on k-means clustering, Q-learning, genetic algorithms, and/or association rules. In particular, a neural network can be a deep neural network, a convolutional neural network, or a convolutional deep neural network. Furthermore, a neural network can be an adversarial network, a deep adversarial network and/or a generative adversarial network.

Figure 8:
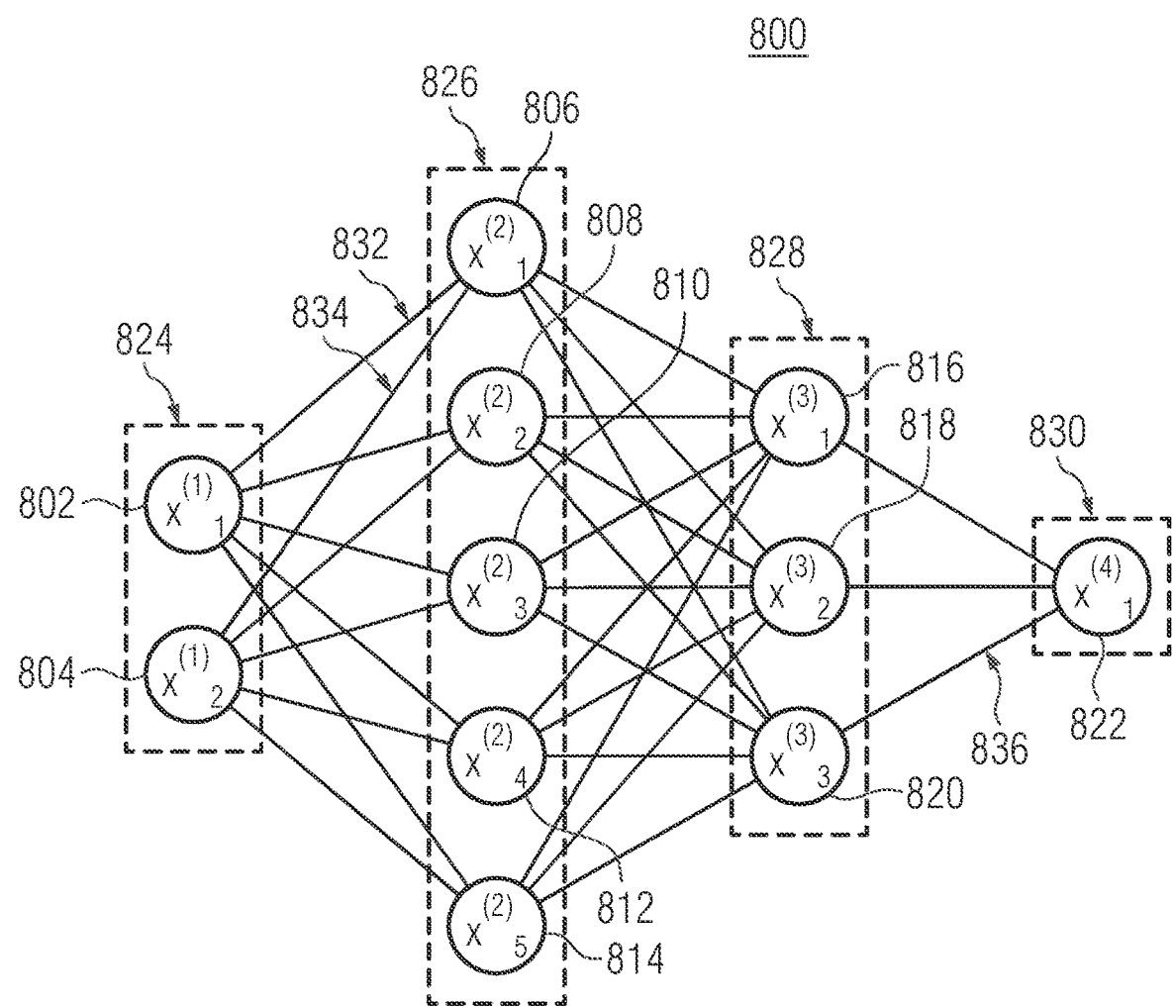
FIG. 8 shows an exemplary artificial neural network that may be used to implement one or more embodiments.

FIG. 8 shows an embodiment of an artificial neural network 800, in accordance with one or more embodiments. Alternative terms for "artificial neural network" are "neural network", "artificial neural net" or "neural net". Machine learning networks described herein, such as, e.g., the encoder network described with respect to method 100 of FIG. 1, the encoder network $f_\theta$ 212 of framework 200 of FIG. 2, the encoder network described with respect to method 300 of FIG. 3, and central model 710 of framework 700 of FIG. 7, may be implemented using artificial neural network 800.

The artificial neural network 800 comprises nodes 802-822 and edges 832, 834, . . . , 836, wherein each edge 832, 834, . . . , 836 is a directed connection from a first node 802-822 to a second node 802-822. In general, the first node 802-822 and the second node 802-822 are different nodes 802-822, it is also possible that the first node 802-822 and the second node 802-822 are identical. For example, in FIG. 8, the edge 832 is a directed connection from the node 802 to the node 806, and the edge 834 is a directed connection from the node 804 to the node 806. An edge 832, 834, . . . , 836 from a first node 802-822 to a second node 802-822 is also denoted as "ingoing edge" for the second node 802-822 and as "outgoing edge" for the first node 802-822.

In this embodiment, the nodes 802-822 of the artificial neural network 800 can be arranged in layers 824-830, wherein the layers can comprise an intrinsic order introduced by the edges 832, 834, . . . , 836 between the nodes 802-822. In particular, edges 832, 834, . . . , 836 can exist only between neighboring layers of nodes. In the embodiment shown in FIG. 8, there is an input layer 824 comprising only nodes 802 and 804 without an incoming edge, an output layer 830 comprising only node 822 without outgoing edges, and hidden layers 826, 828 in-between the input layer 824 and the output layer 830. In general, the number of hidden layers 826, 828 can be chosen arbitrarily. The number of nodes 802 and 804 within the input layer 824 usually relates to the number of input values of the neural network 800, and the number of nodes 822 within the output layer 830 usually relates to the number of output values of the neural network 800.

In particular, a (real) number can be assigned as a value to every node 802-822 of the neural network 800. Here, $x^{(n)}_i$ denotes the value of the i-th node 802-822 of the n-th layer 824-830. The values of the nodes 802-822 of the input layer 824 are equivalent to the input values of the neural network 800, the value of the node 822 of the output layer 830 is equivalent to the output value of the neural network 800. Furthermore, each edge 832, 834, . . . , 836 can comprise a weight being a real number, in particular, the weight is a real number within the interval [−1, 1] or within the interval [0, 1]. Here, $w^{(m,n)}_{i,j}$ denotes the weight of the edge between the i-th node 802-822 of the m-th layer 824-830 and the j-th node 802-822 of the n-th layer 824-830. Furthermore, the abbreviation $w(n)_{i,j}$ is defined for the weight $w^{(n,n+1)}_{i,j}$.

In particular, to calculate the output values of the neural network 800, the input values are propagated through the neural network. In particular, the values of the nodes 802-822 of the (n+1)-th layer 824-830 can be calculated based on the values of the nodes 802-822 of the n-th layer 824-830 by $$x_j^{(n+1)} = f\left(\sum_i x_i^{(n)} \cdot w_{i,j}^{(n)}\right).$$

Herein, the function f is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions. The transfer function is mainly used for normalization purposes.

In particular, the values are propagated layer-wise through the neural network, wherein values of the input layer 824 are given by the input of the neural network 800, wherein values of the first hidden layer 826 can be calculated based on the values of the input layer 824 of the neural network, wherein values of the second hidden layer 828 can be calculated based in the values of the first hidden layer 826, etc.

In order to set the values $w^{(m,n)}_{i,j}$ for the edges, the neural network 800 has to be trained using training data. In particular, training data comprises training input data and training output data (denoted as $t_i$). For a training step, the neural network 800 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 800 (backpropagation algorithm). In particular, the weights are changed according to $$w_{i,j}^{\prime(n)} = w_{i,j}^{(n)} - \gamma \cdot \delta_j^{(n)} \cdot x_i^{(n)}$$

wherein $\gamma$ is a learning rate, and the numbers $\delta^{(n)}_j$ can be recursively calculated as $$\delta_j^{(n)} = \left(\sum_k \delta_k^{(n+1)} \cdot w_{j,k}^{(n+1)}\right) \cdot f'\left(\sum_i x_i^{(n)} \cdot w_{i,j}^{(n)}\right)$$

based on $\delta^{(n+1)}_j$, if the (n+1)-th layer is not the output layer, and $$\delta_j^{(n)} = (x_k^{(n+1)} - t_j^{(n+1)}) \cdot f'\left(\sum_i x_i^{(n)} \cdot w_{i,j}^{(n)}\right)$$

if the (n+1)-th layer is the output layer 830, wherein f' is the first derivative of the activation function, and $y^{(n+1)}_j$ is the comparison training value for the j-th node of the output layer 830.

Figure 9:
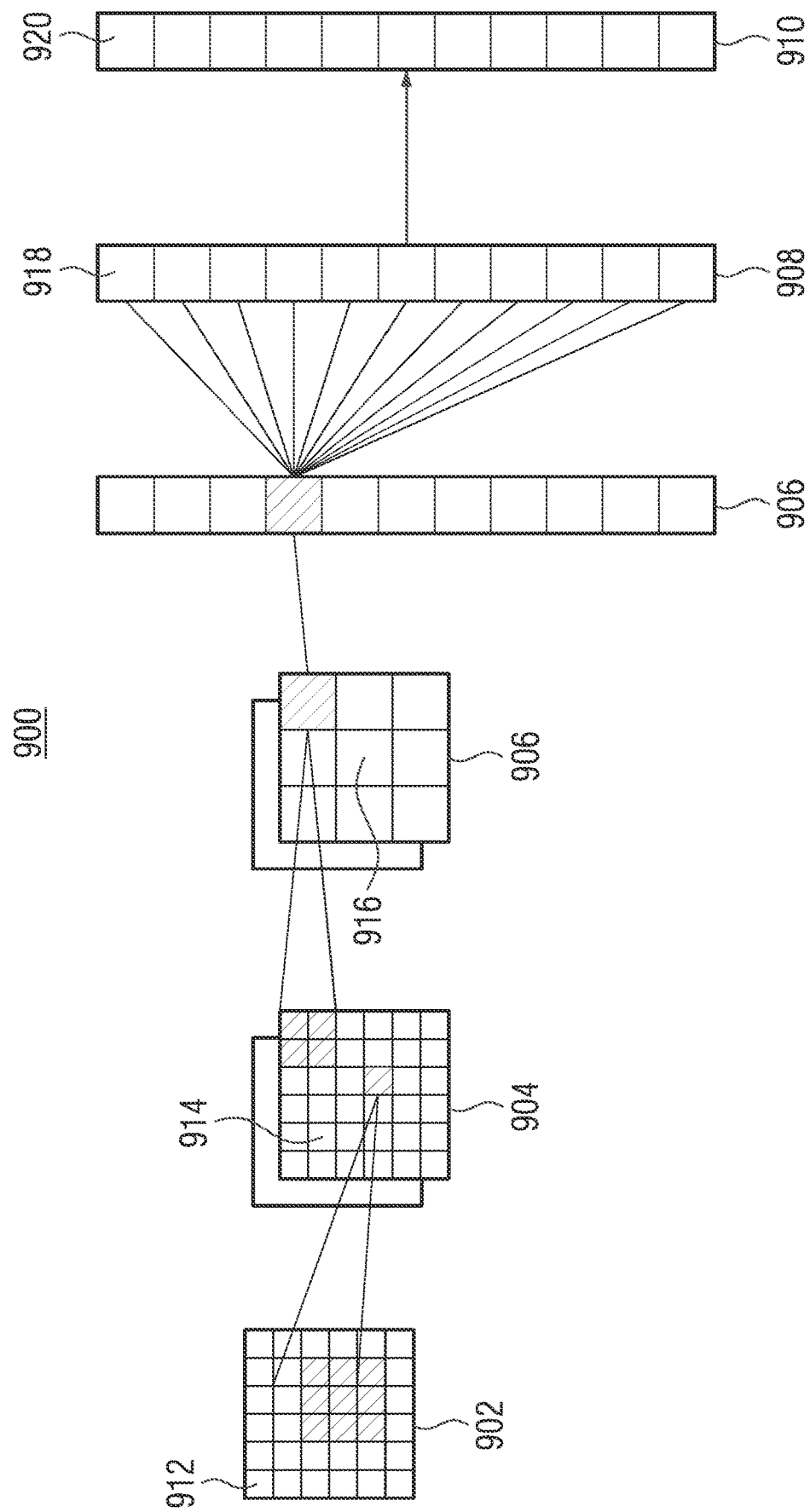
FIG. 9 shows a convolutional neural network that may be used to implement one or more embodiments.

FIG. 9 shows a convolutional neural network 900, in accordance with one or more embodiments. Machine learning networks described herein, such as, e.g., the encoder network described with respect to method 100 of FIG. 1, the encoder network $f_\theta$ 212 of framework 200 of FIG. 2, the encoder network described with respect to method 300 of FIG. 3, and central model 710 of framework 700 of FIG. 7, may be implemented using convolutional neural network 900.

In the embodiment shown in FIG. 9, the convolutional neural network comprises 900 an input layer 902, a convolutional layer 904, a pooling layer 906, a fully connected layer 908, and an output layer 910. Alternatively, the convolutional neural network 900 can comprise several convolutional layers 904, several pooling layers 906, and several fully connected layers 908, as well as other types of layers.

The order of the layers can be chosen arbitrarily, usually fully connected layers 908 are used as the last layers before the output layer 910.

In particular, within a convolutional neural network 900, the nodes 912-920 of one layer 902-910 can be considered to be arranged as a d-dimensional matrix or as a d-dimensional image. In particular, in the two-dimensional case the value of the node 912-920 indexed with i and j in the n-th layer 902-910 can be denoted as $x^{(n)}_{[i,j]}$. However, the arrangement of the nodes 912-920 of one layer 902-910 does not have an effect on the calculations executed within the convolutional neural network 900 as such, since these are given solely by the structure and the weights of the edges.

In particular, a convolutional layer 904 is characterized by the structure and the weights of the incoming edges forming a convolution operation based on a certain number of kernels. In particular, the structure and the weights of the incoming edges are chosen such that the values $x^{(n)}_k$ of the nodes 914 of the convolutional layer 904 are calculated as a convolution $x^{(n)}_k = K_k * x^{(n-1)}$ based on the values $x^{(n-1)}$ of the nodes 912 of the preceding layer 902, where the convolution * is defined in the two-dimensional case as $$x_k^{(n)}[i,j]=(K_k * x^{(n-1)})[i,j]=\Sigma_i \Sigma_j K_k[i',j'] \cdot x^{(n-1)}[i-i',j-j'].$$

Here the k-th kernel $K_k$ is a d-dimensional matrix (in this embodiment a two-dimensional matrix), which is usually small compared to the number of nodes 912-918 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 912-920 in the respective layer 902-910. In particular, for a convolutional layer 904, the number of nodes 914 in the convolutional layer is equivalent to the number of nodes 912 in the preceding layer 902 multiplied with the number of kernels.

If the nodes 912 of the preceding layer 902 are arranged as a d-dimensional matrix, using a plurality of kernels can be interpreted as adding a further dimension (denoted as "depth" dimension), so that the nodes 914 of the convolutional layer 904 are arranged as a (d+1)-dimensional matrix. If the nodes 912 of the preceding layer 902 are already arranged as a (d+1)-dimensional matrix comprising a depth dimension, using a plurality of kernels can be interpreted as expanding along the depth dimension, so that the nodes 914 of the convolutional layer 904 are arranged also as a (d+1)-dimensional matrix, wherein the size of the (d+1)-dimensional matrix with respect to the depth dimension is by a factor of the number of kernels larger than in the preceding layer 902.

The advantage of using convolutional layers 904 is that spatially local correlation of the input data can exploited by enforcing a local connectivity pattern between nodes of adjacent layers, in particular by each node being connected to only a small region of the nodes of the preceding layer.

In embodiment shown in FIG. 9, the input layer 902 comprises 36 nodes 912, arranged as a two-dimensional 6×6 matrix. The convolutional layer 904 comprises 72 nodes 914, arranged as two two-dimensional 6×6 matrices, each of the two matrices being the result of a convolution of the values of the input layer with a kernel. Equivalently, the nodes 914 of the convolutional layer 904 can be interpreted as arranges as a three-dimensional 6×6×2 matrix, wherein the last dimension is the depth dimension.

A pooling layer 906 can be characterized by the structure and the weights of the incoming edges and the activation function of its nodes 916 forming a pooling operation based on a non-linear pooling function f. For example, in the two dimensional case the values $x^{(n)}$ of the nodes 916 of the pooling layer 906 can be calculated based on the values $x^{(n-1)}$ of the nodes 914 of the preceding layer 904 as $$x^{(n)}[i,j]=f(x^{(n-1)}[id_1,jd_2], \ldots, x^{(n-1)}[id_1+d_1-1,jd_2+d_2-1])$$

In other words, by using a pooling layer 906, the number of nodes 914, 916 can be reduced, by replacing a number d1·d2 of neighboring nodes 914 in the preceding layer 904 with a single node 916 being calculated as a function of the values of said number of neighboring nodes in the pooling layer. In particular, the pooling function f can be the max-function, the average or the L2-Norm. In particular, for a pooling layer 906 the weights of the incoming edges are fixed and are not modified by training.

The advantage of using a pooling layer 906 is that the number of nodes 914, 916 and the number of parameters is reduced. This leads to the amount of computation in the network being reduced and to a control of overfitting.

In the embodiment shown in FIG. 9, the pooling layer 906 is a max-pooling, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

A fully-connected layer 908 can be characterized by the fact that a majority, in particular, all edges between nodes 916 of the previous layer 906 and the nodes 918 of the fully-connected layer 908 are present, and wherein the weight of each of the edges can be adjusted individually.

In this embodiment, the nodes 916 of the preceding layer 906 of the fully-connected layer 908 are displayed both as two-dimensional matrices, and additionally as non-related nodes (indicated as a line of nodes, wherein the number of nodes was reduced for a better presentability). In this embodiment, the number of nodes 918 in the fully connected layer 908 is equal to the number of nodes 916 in the preceding layer 906. Alternatively, the number of nodes 916, 918 can differ.

Furthermore, in this embodiment, the values of the nodes 920 of the output layer 910 are determined by applying the Softmax function onto the values of the nodes 918 of the preceding layer 908. By applying the Softmax function, the sum the values of all nodes 920 of the output layer 910 is 1, and all values of all nodes 920 of the output layer are real numbers between 0 and 1.

A convolutional neural network 900 can also comprise a ReLU (rectified linear units) layer or activation layers with non-linear transfer functions. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer.

The input and output of different convolutional neural network blocks can be wired using summation (residual/dense neural networks), element-wise multiplication (attention) or other differentiable operators. Therefore, the convolutional neural network architecture can be nested rather than being sequential if the whole pipeline is differentiable.

In particular, convolutional neural networks 900 can be trained based on the backpropagation algorithm. For preventing overfitting, methods of regularization can be used, e.g. dropout of nodes 912-920, stochastic pooling, use of artificial data, weight decay based on the L1 or the L2 norm, or max norm constraints. Different loss functions can be combined for training the same neural network to reflect the joint training objectives. A subset of the neural network parameters can be excluded from optimization to retain the weights pretrained on another datasets.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIGS. 1-3. Certain steps or functions of the methods and workflows described herein, including one or more of the steps or functions of FIGS. 1-3, may be performed by a server or by another processor in a network-based cloud-computing system. Certain steps or functions of the methods and workflows described herein, including one or more of the steps of FIGS. 1-3, may be performed by a client computer in a network-based cloud computing system. The steps or functions of the methods and workflows described herein, including one or more of the steps of FIGS. 1-3, may be performed by a server and/or by a client computer in a network-based cloud computing system, in any combination.

Figure 2:
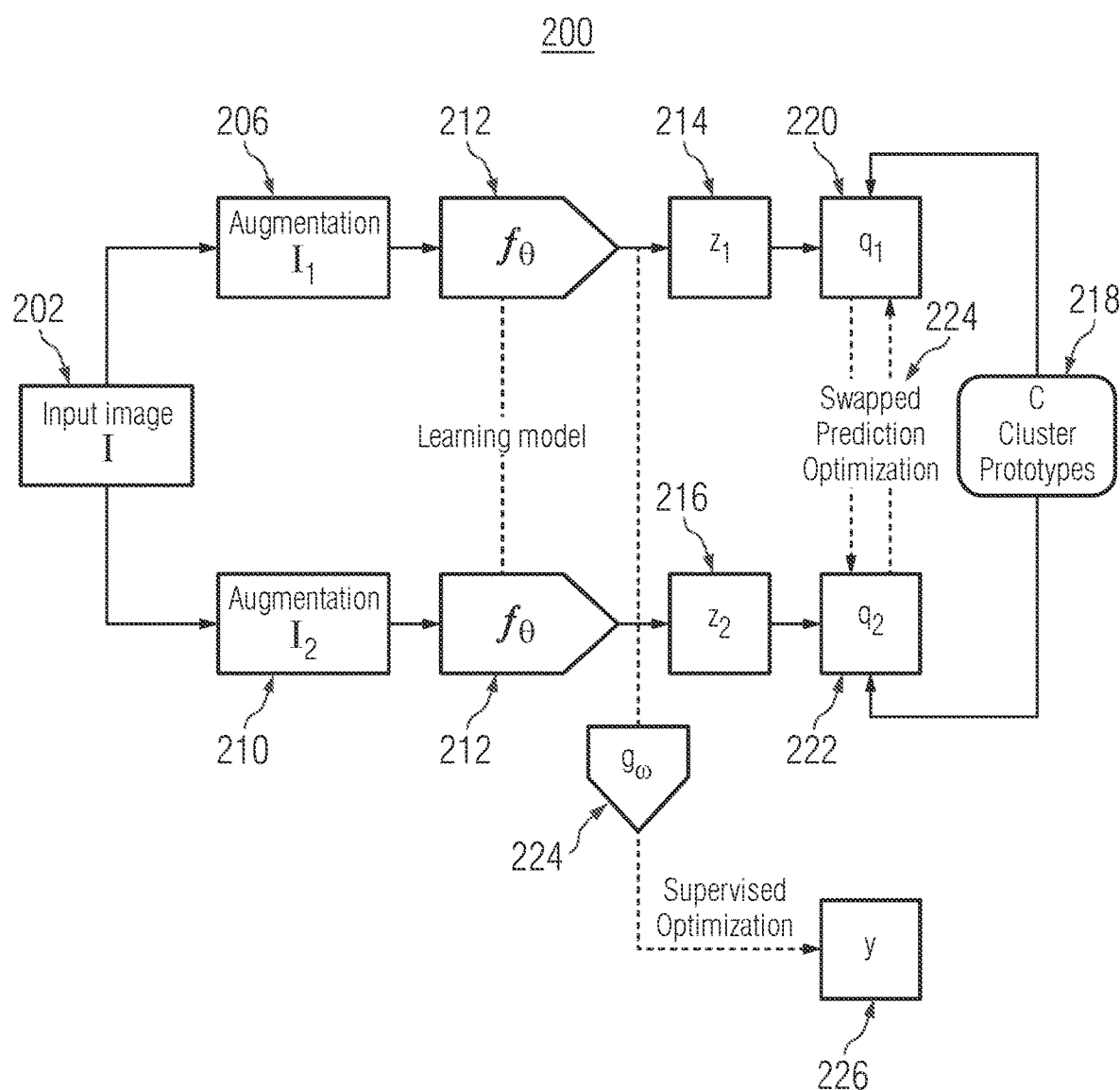
FIG. 2 shows a framework for self-supervised learning for training an artificial intelligence-based system, in accordance with one or more embodiments.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIGS. 1-3, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 10:
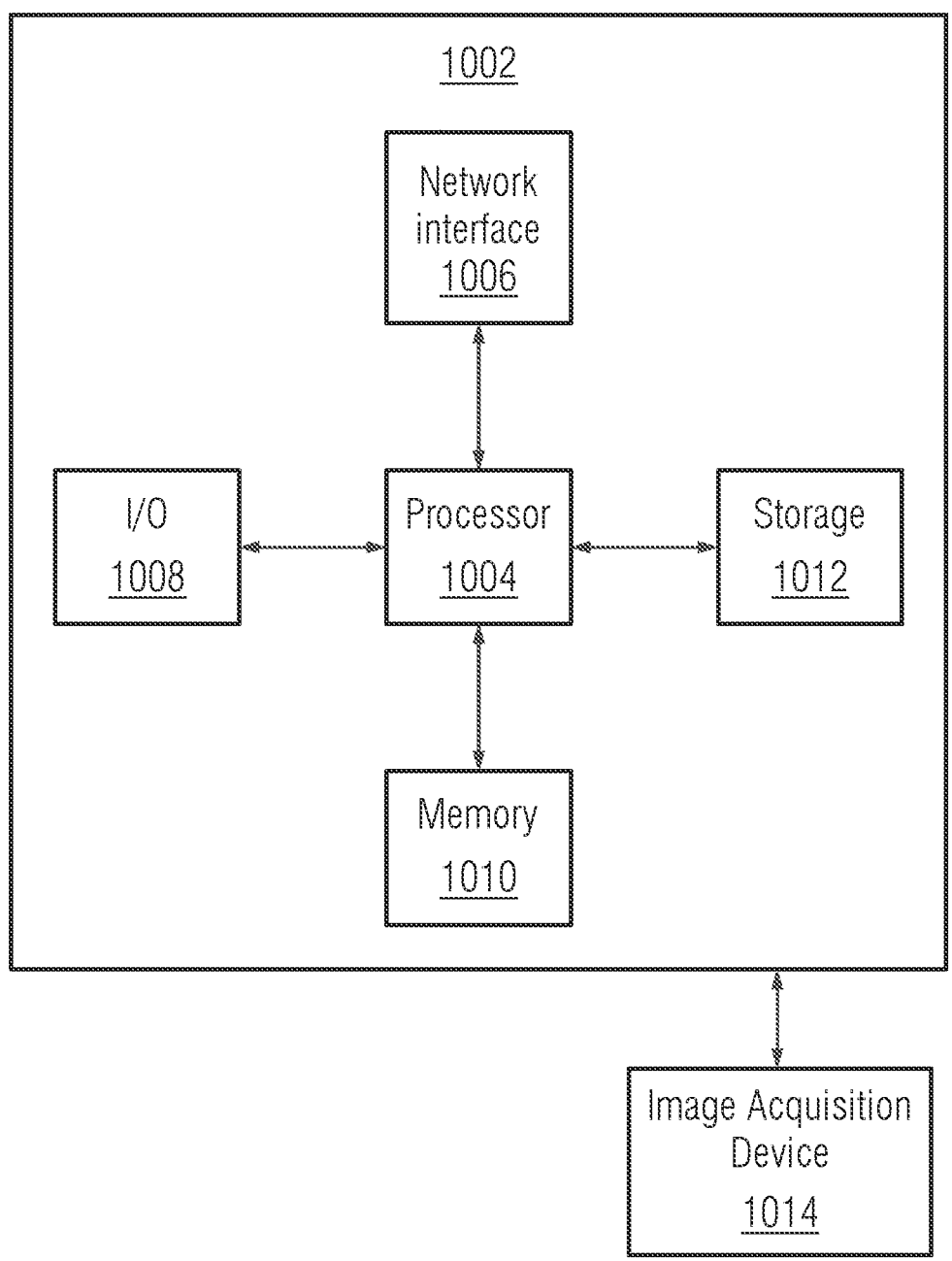
FIG. 10 shows a high-level block diagram of a computer that may be used to implement one or more embodiments.

A high-level block diagram of an example computer 1002 that may be used to implement systems, apparatus, and methods described herein is depicted in FIG. 10. Computer 1002 includes a processor 1004 operatively coupled to a data storage device 1012 and a memory 1010. Processor 1004 controls the overall operation of computer 1002 by executing computer program instructions that define such operations. The computer program instructions may be stored in data storage device 1012, or other computer readable medium, and loaded into memory 1010 when execution of the computer program instructions is desired. Thus, the method and workflow steps or functions of FIGS. 1-3 can be defined by the computer program instructions stored in memory 1010 and/or data storage device 1012 and controlled by processor 1004 executing the computer program instructions. For example, the computer program instructions can be implemented as computer executable code programmed by one skilled in the art to perform the method and workflow steps or functions of FIGS. 1-3. Accordingly, by executing the computer program instructions, the processor 1004 executes the method and workflow steps or functions of FIGS. 1-3. Computer 1002 may also include one or more network interfaces 1006 for communicating with other devices via a network. Computer 1002 may also include one or more input/output devices 1008 that enable user interaction with computer 1002 (e.g., display, keyboard, mouse, speakers, buttons, etc.).

Processor 1004 may include both general and special purpose microprocessors, and may be the sole processor or one of multiple processors of computer 1002. Processor 1004 may include one or more central processing units (CPUs), for example. Processor 1004, data storage device 1012, and/or memory 1010 may include, be supplemented by, or incorporated in, one or more application-specific integrated circuits (ASICs) and/or one or more field programmable gate arrays (FPGAs).

Data storage device 1012 and memory 1010 each include a tangible non-transitory computer readable storage medium. Data storage device 1012, and memory 1010, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 1008 may include peripherals, such as a printer, scanner, display screen, etc. For example, input/output devices 1008 may include a display device such as a cathode ray tube (CRT) or liquid crystal display (LCD)

monitor for displaying information to the user, a keyboard, and a pointing device such as a mouse or a trackball by which the user can provide input to computer 1002.

An image acquisition device 1014 can be connected to the computer 1002 to input image data (e.g., medical images) to the computer 1002. It is possible to implement the image acquisition device 1014 and the computer 1002 as one device. It is also possible that the image acquisition device 1014 and the computer 1002 communicate wirelessly through a network. In a possible embodiment, the computer 1002 can be located remotely with respect to the image acquisition device 1014.

Any or all of the systems and apparatus discussed herein may be implemented using one or more computers such as computer 1002.

One skilled in the art will recognize that an implementation of an actual computer or computer system may have other structures and may contain other components as well, and that FIG. 10 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A computer-implemented method comprising:
   for each respective training medical image of a set of unannotated training medical images:
   generating a first augmented image by applying a first augmentation operation to the respective training medical image,
   generating a second augmented image by applying a second augmentation operation to the respective training medical image,
   creating a first representation vector from the first augmented image using an encoder network,
   creating a second representation vector from the second augmented image using the encoder network,
   mapping the first representation vector to first cluster codes, and
   mapping the second representation vector to second cluster codes; and
   optimizing the encoder network by 1) calculating a first loss based on the first representation vectors and the second cluster codes and 2) calculating a second loss based on the second representation vectors and the first cluster codes.

2. The computer-implemented method of claim 1, wherein optimizing the encoder network by 1) calculating the first loss based on the first representation vectors and the second cluster codes and 2) calculating the second loss based on the second representation vectors and the first cluster codes comprises:
   optimizing the encoder network to find cluster codes that maximize a similarity between representation vectors and cluster prototypes.

3. The computer-implemented method of claim 1, wherein optimizing the encoder network by 1) calculating the first loss based on the first representation vectors and the second cluster codes and 2) calculating the second loss based on the second representation vectors and the first cluster codes comprises:
   optimizing the encoder network further by combining the first loss and the second loss.

4. The computer-implemented method of claim 1, wherein optimizing the encoder network by 1) calculating the first loss based on the first representation vectors and the second cluster codes and 2) calculating the second loss based on the second representation vectors and the first cluster codes comprises:
   optimizing a loss function by clustering based on a modality of each of the training medical images.

5. The computer-implemented method of claim 1, wherein one of the first augmentation operation or the second augmentation operation comprises an energy-based augmentation performed by:
   decomposing an image into a plurality of energy bands;
   computing an energy value for each of the plurality of energy bands; and
   transforming the image based on the energy values.

6. The computer-implemented method of claim 1, wherein the set of unannotated training medical images comprises a plurality of subsets of training medical images each associated with different sites, and wherein optimizing the encoder network by 1) calculating the first loss based on the first representation vectors and the second cluster codes and 2) calculating the second loss based on the second representation vectors and the first cluster codes comprises:
   continuously optimizing the encoder network with the plurality of subsets of training medical images using federated learning and continual learning.

7. The computer-implemented method of claim 1, further comprising
   receiving annotated training data comprising annotated training medical images and corresponding annotations; and
   mapping the annotated training medical images to predicted annotations using a machine learning based network based on features of the encoder network,
   wherein optimizing the encoder network by 1) calculating the first loss based on the first representation vectors and the second cluster codes and 2) calculating the second loss based on the second representation vectors and the first cluster codes comprises optimizing the encoder network to minimize a distance of the predicted annotations to the corresponding annotations.

8. The computer-implemented method of claim 1, further comprising:
   receiving an input medical image;
   creating a representation vector from the input medical image using the optimized encoder network;
   performing a medical imaging analysis task for the input medical image based on the representation vector; and
   outputting results of the medical imaging analysis task.

9. The computer-implemented method of claim 8, wherein performing a medical imaging analysis task for the input medical image based on the representation vector comprises:
   decoding the representation vector using a decoder network to perform the medical imaging analysis task.

10. An apparatus comprising:
    for each respective training medical image of a set of unannotated training medical images:

means for generating a first augmented image by applying a first augmentation operation to the respective training medical image,
means for generating a second augmented image by applying a second augmentation operation to the respective training medical image,
means for creating a first representation vector from the first augmented image using an encoder network,
means for creating a second representation vector from the second augmented image using the encoder network,
means for mapping the first representation vector to first cluster codes, and
means for mapping the second representation vector to second cluster codes; and
means for optimizing the encoder network by 1) calculating a first loss based on the first representation vectors and the second cluster codes and 2) calculating a second loss based on the second representation vectors and the first cluster codes according to a contrastive loss function using the first and second representation vectors and the first and second cluster codes.

11. The apparatus of claim 10, wherein the means for optimizing the encoder network by 1) calculating the first loss based on the first representation vectors and the second cluster codes and 2) calculating the second loss based on the second representation vectors and the first cluster codes comprises:
means for optimizing the encoder network to find cluster codes that maximize a similarity between representation vectors and cluster prototypes.

12. The apparatus of claim 10, wherein the means for optimizing the encoder network by 1) calculating the first loss based on the first representation vectors and the second cluster codes and 2) calculating the second loss based on the second representation vectors and the first cluster codes comprises:
means for optimizing the encoder network further by combining the first loss and the second loss.

13. The apparatus of claim 10, wherein the means for optimizing the encoder network by 1) calculating the first loss based on the first representation vectors and the second cluster codes and 2) calculating the second loss based on the second representation vectors and the first cluster codes comprises:
means for optimizing a loss function by clustering based on a modality of each of the training medical images.

14. The apparatus of claim 10, wherein one of the first augmentation operation or the second augmentation operation comprises an energy-based augmentation performed by:
means for decomposing an image into a plurality of energy bands;
means for computing an energy value for each of the plurality of energy bands; and
means for transforming the image based on the energy values.

15. A non-transitory computer readable medium storing computer program instructions, the computer program instructions when executed by a processor cause the processor to perform operations comprising:
for each respective training medical image of a set of unannotated training medical images:
generating a first augmented image by applying a first augmentation operation to the respective training medical image,
generating a second augmented image by applying a second augmentation operation to the respective training medical image,
creating a first representation vector from the first augmented image using an encoder network,
creating a second representation vector from the second augmented image using the encoder network,
mapping the first representation vector to first cluster codes, and
mapping the second representation vector to second cluster codes; and
optimizing the encoder network by 1) calculating a first loss based on the first representation vectors and the second cluster codes and 2) calculating a second loss based on the second representation vectors and the first cluster codes.

16. The non-transitory computer readable medium of claim 15, wherein optimizing the encoder network by 1) calculating the first loss based on the first representation vectors and the second cluster codes and 2) calculating the second loss based on the second representation vectors and the first cluster codes comprises:
optimizing the encoder network to find cluster codes that maximize a similarity between representation vectors and cluster prototypes.

17. The non-transitory computer readable medium of claim 15, wherein the set of unannotated training medical images comprises a plurality of subsets of training medical images each associated with different sites, and wherein optimizing the encoder network by 1) calculating the first loss based on the first representation vectors and the second cluster codes and 2) calculating the second loss based on the second representation vectors and the first cluster codes comprises:
continuously optimizing the encoder network with the plurality of subsets of training medical images using federated learning and continual learning.

18. The non-transitory computer readable medium of claim 15, the operations further comprising
receiving annotated training data comprising annotated training medical images and corresponding annotations; and
mapping the annotated training medical images to predicted annotations using a machine learning based network based on features of the encoder network,
wherein optimizing the encoder network by 1) calculating the first loss based on the first representation vectors and the second cluster codes and 2) calculating the second loss based on the second representation vectors and the first cluster codes comprises optimizing the encoder network to minimize a distance of the predicted annotations to the corresponding annotations.

19. The non-transitory computer readable medium of claim 15, the operations further comprising:
receiving an input medical image;
creating a representation vector from the input medical image using the optimized encoder network;
performing a medical imaging analysis task for the input medical image based on the representation vector; and
outputting results of the medical imaging analysis task.

20. The non-transitory computer readable medium of claim 19, wherein performing a medical imaging analysis task for the input medical image based on the representation vector comprises:

decoding the representation vector using a decoder network to perform the medical imaging analysis task.

* * * * *